(12) United States Patent
Saint

(10) Patent No.: US 9,486,171 B2
(45) Date of Patent: Nov. 8, 2016

(54) PREDICTIVE CALIBRATION

(71) Applicant: Tandem Diabetes Care, Inc., San Diego, CA (US)

(72) Inventor: Sean Saint, San Diego, CA (US)

(73) Assignee: Tandem Diabetes Care, Inc., San Diego, CA (US)

(*) Notice: Subject to any disclaimer, the term of this patent is extended or adjusted under 35 U.S.C. 154(b) by 712 days.

(21) Appl. No.: 13/841,028

(22) Filed: Mar. 15, 2013

(65) Prior Publication Data
US 2014/0273042 A1 Sep. 18, 2014

(51) Int. Cl.
*A61B 5/00* (2006.01)
*A61B 5/145* (2006.01)

(52) U.S. Cl.
CPC ......... *A61B 5/7275* (2013.01); *A61B 5/14532* (2013.01); *A61B 2560/0223* (2013.01)

(58) Field of Classification Search
CPC .................................................. A61B 5/7275
USPC .............................................................. 702/23
See application file for complete search history.

(56) References Cited

U.S. PATENT DOCUMENTS

| | | | |
|---|---|---|---|
| 6,083,710 A | 7/2000 | Heller et al. |
| 6,175,752 B1 | 1/2001 | Say et al. |
| 6,233,471 B1 | 5/2001 | Berner et al. |
| 6,248,067 B1 | 6/2001 | Causey et al. |
| 6,514,689 B2 | 2/2003 | Han et al. |
| 6,546,269 B1 | 4/2003 | Kurnik |
| 6,558,320 B1 | 5/2003 | Causey et al. |
| 6,561,978 B1 | 5/2003 | Conn et al. |
| 6,565,509 B1 | 5/2003 | Say et al. |
| 6,595,919 B2 | 7/2003 | Berner et al. |
| 6,641,533 B2 | 11/2003 | Causey et al. |
| 6,752,787 B1 | 6/2004 | Causey et al. |
| 6,923,764 B2 | 8/2005 | Aceti et al. |
| 7,004,928 B2 | 2/2006 | Aceti et al. |
| 7,011,630 B2 | 3/2006 | Desai et al. |
| 7,295,867 B2 | 11/2007 | Berner et al. |
| 7,399,401 B2 | 7/2008 | Rush |
| 7,405,055 B2 | 7/2008 | Dunn et al. |
| 7,618,369 B2 | 11/2009 | Hayter et al. |
| 7,630,748 B2 | 12/2009 | Budiman |
| 7,653,425 B2 | 1/2010 | Hayter et al. |
| 7,697,967 B2 | 4/2010 | Stafford |
| 7,699,775 B2 | 4/2010 | Desai et al. |
| 7,713,574 B2 | 5/2010 | Brister et al. |
| 7,715,893 B2 | 5/2010 | Kamath et al. |
| 7,768,386 B2 | 8/2010 | Hayter et al. |
| 7,774,145 B2 | 8/2010 | Brauker et al. |
| 7,775,975 B2 | 8/2010 | Brister et al. |
| 7,778,680 B2 | 8/2010 | Goode, Jr. et al. |
| 7,797,028 B2 | 9/2010 | Goode, Jr. et al. |
| 7,826,382 B2 | 11/2010 | Sicurello et al. |
| 7,831,287 B2 | 11/2010 | Brister et al. |
| 7,860,544 B2 | 12/2010 | Say et al. |
| 7,869,853 B1 | 1/2011 | Say et al. |
| 7,885,699 B2 | 2/2011 | Say et al. |
| 7,914,450 B2 | 3/2011 | Goode, Jr. et al. |
| 7,914,742 B2 | 3/2011 | Arbogast et al. |
| 7,917,186 B2 | 3/2011 | Kamath et al. |
| 7,920,907 B2 | 4/2011 | Mcgarraugh et al. |
| 7,925,321 B2 | 4/2011 | Goode et al. |
| 7,928,850 B2 | 4/2011 | Hayter et al. |
| 7,933,639 B2 | 4/2011 | Goode et al. |
| 7,955,261 B2 | 6/2011 | Goode et al. |
| 7,959,569 B2 | 6/2011 | Goode et al. |
| 7,979,104 B2 | 7/2011 | Kamath et al. |
| 7,981,034 B2 | 7/2011 | Jennewine et al. |
| 7,986,986 B2 | 7/2011 | Goode et al. |
| 7,996,158 B2 | 8/2011 | Hayter et al. |
| 8,000,763 B2 | 8/2011 | Mazza et al. |
| 8,005,524 B2 | 8/2011 | Brauker et al. |
| 8,052,601 B2 | 11/2011 | Goode, Jr. et al. |
| 8,121,857 B2 | 2/2012 | Galasso et al. |
| 8,149,117 B2 | 4/2012 | Fennell et al. |
| 8,177,716 B2 | 5/2012 | Say et al. |
| 8,206,296 B2 | 6/2012 | Jennewine |
| 8,226,558 B2 | 7/2012 | Say et al. |
| 8,251,906 B2 | 8/2012 | Brauker et al. |
| 8,257,259 B2 | 9/2012 | Brauker et al. |
| 8,280,476 B2 | 10/2012 | Jina |
| 8,287,454 B2 | 10/2012 | Wolpert et al. |
| 8,290,562 B2 | 10/2012 | Goode, Jr. et al. |
| 8,303,518 B2 | 11/2012 | Aceti et al. |
| 8,332,008 B2 | 12/2012 | Goode et al. |
| 8,357,091 B2 | 1/2013 | Say et al. |
| 8,369,919 B2 | 2/2013 | Kamath et al. |
| 8,377,031 B2 | 2/2013 | Hayter et al. |
| 8,380,273 B2 | 2/2013 | Say et al. |
| 8,409,131 B2 | 4/2013 | Say et al. |
| 8,461,985 B2 | 6/2013 | Fennell et al. |
| 8,579,853 B2 | 11/2013 | Reggiardo et al. |
| 2001/0041869 A1 | 11/2001 | Causey et al. |
| 2004/0073095 A1 | 4/2004 | Causey et al. |
| 2007/0060869 A1 | 3/2007 | Tolle et al. |
| 2007/0060870 A1 | 3/2007 | Tolle et al. |
| 2007/0093786 A1 | 4/2007 | Goldsmith et al. |
| 2007/0100222 A1 | 5/2007 | Mastrototaro et al. |
| 2007/0156033 A1 | 7/2007 | Causey et al. |
| 2008/0004601 A1 | 1/2008 | Jennewine et al. |
| 2009/0112478 A1* | 4/2009 | Mueller, Jr. ....... A61B 5/14532 702/19 |
| 2009/0143661 A1 | 6/2009 | Taub et al. |
| 2009/0171269 A1 | 7/2009 | Jennewine et al. |
| 2009/0192366 A1 | 7/2009 | Mensinger et al. |
| 2009/0192724 A1 | 7/2009 | Brauker et al. |
| 2009/0192745 A1 | 7/2009 | Kamath et al. |
| 2009/0227855 A1 | 9/2009 | Hill et al. |

(Continued)

*Primary Examiner* — Jerry Lin
(74) *Attorney, Agent, or Firm* — Patterson Thuente Pedersen, P.A.

(57) ABSTRACT

A portable medical monitor system generates a current calibration curve for generating the estimate of the level of an analyte, such as glucose, being monitored. The current calibration curve is based on at least two measured data values of the level being monitored. The system determines a transformation function based on the calibration curve and at least one preceding calibration curve such that the transformation function produces a predictive calibration curve, and generates an estimated level value of the level being monitored, based on sensor output from a sensor associated with the portable medical monitor system, in accordance with the predictive calibration curve.

30 Claims, 10 Drawing Sheets

(56) References Cited

U.S. PATENT DOCUMENTS

| | | |
|---|---|---|
| 2009/0240193 A1 | 9/2009 | Mensinger et al. |
| 2010/0121169 A1 | 5/2010 | Petisce et al. |
| 2010/0164727 A1 | 7/2010 | Bazargan et al. |
| 2010/0168543 A1 | 7/2010 | Kamath et al. |
| 2010/0168711 A1 | 7/2010 | Bazargan et al. |
| 2010/0179402 A1 | 7/2010 | Goode et al. |
| 2010/0198034 A1 | 8/2010 | Thomas et al. |
| 2010/0198142 A1 | 8/2010 | Sloan et al. |
| 2010/0234709 A1 | 9/2010 | Say et al. |
| 2010/0274515 A1 | 10/2010 | Hoss et al. |
| 2010/0298681 A1 | 11/2010 | Say et al. |
| 2011/0015505 A1* | 1/2011 | Schurman ............ A61B 5/0066 600/310 |
| 2011/0044333 A1 | 2/2011 | Sicurello et al. |
| 2011/0056264 A1 | 3/2011 | Kaplan et al. |
| 2011/0077481 A1 | 3/2011 | Say et al. |
| 2011/0120206 A1 | 5/2011 | Troughton et al. |
| 2011/0126188 A1 | 5/2011 | Bernstein et al. |
| 2011/0184264 A1 | 7/2011 | Galasso et al. |
| 2011/0190614 A1 | 8/2011 | Brister et al. |
| 2011/0213225 A1 | 9/2011 | Bernstein et al. |
| 2011/0256024 A1 | 10/2011 | Cole et al. |
| 2011/0257895 A1 | 10/2011 | Brauker et al. |
| 2012/0232520 A1 | 9/2012 | Sloan et al. |
| 2014/0012511 A1 | 1/2014 | Mensinger et al. |
| 2014/0276419 A1 | 9/2014 | Rosinko et al. |

* cited by examiner (Predictive Calibration)

PREDICTIVE CALIBRATION

CROSS-REFERENCES TO RELATED APPLICATIONS

This application hereby incorporates by reference in its entirety each of the following commonly-owned patents and patent applications: U.S. patent application Ser. No. 12/846,688 entitled "Infusion Pump System with Disposable Cartridge Having Pressure Venting and Pressure Feedback" filed Jul. 29, 2010 by P. DiPerna et al.; U.S. patent application Ser. No. 12/846,720 entitled "Infusion Pump System with Disposable Cartridge Having Pressure Venting and Pressure Feedback" filed Jul. 29, 2010 by P. DiPerna et al.; U.S. patent application Ser. No. 12/846,734 entitled "Infusion Pump System with Disposable Cartridge Having Pressure Venting and Pressure Feedback" filed Jul. 29, 2010 by E. Verhoef et al.; U.S. patent application Ser. No. 12/846,706 entitled "Infusion Pump System with Disposable Cartridge Having Pressure Venting and Pressure Feedback" filed Jul. 29, 2010, by M. Michaud et al.; U.S. patent application Ser. No. 12/846,733 entitled "Infusion Pump System with Disposable Cartridge Having Pressure Venting and Pressure Feedback" filed Jul. 29, 2010 by M. Michaud et al.; PCT Patent Application No. PCT/US2010/043789 entitled "Infusion Pump System with Disposable Cartridge Having Pressure Venting and Pressure Feedback" filed Jul. 29, 2010 by P. DiPerna et al; U.S. patent application Ser. No. 12/714,299 entitled "Methods and Devices for Determination of Flow Reservoir Volume" filed Feb. 26, 2010 by M. Rosinko et al.; U.S. Pat. No. 7,008,403 entitled "Infusion Pump and Method for Use" by S. Mallett; U.S. Pat. No. 7,341,581 entitled "Infusion Pump and Method for Use" by S. Mallet; U.S. Pat. No. 7,374,556 entitled "Infusion Pump and Method for Use" by S. Mallet; U.S. Patent Application Publication No. 2007/0264130 entitled "Infusion Pumps and Method for Use" filed May 4, 2007 by S. Mallett; U.S. Patent Application Publication No. 2009/0191067 entitled "Two Chamber Pumps and Related Methods" filed Jan. 25, 2008 by P. DiPerna; U.S. patent application Ser. No. 13/557,163 entitled "Multi-Reservoir Infusion Pump Systems and Methods" filed Jul. 24, 2012 by P. DiPerna et al.; U.S. patent application Ser. No. 12/538,018 entitled "Two Chamber Pumps and Related Methods" filed Aug. 7, 2009 by P. DiPerna et al.; U.S. patent application Ser. No. 61/656,967 entitled "Sealed Infusion Device with Electrical Connector Port" filed Jun. 7, 2012 by J. Brown et al.; U.S. Pat. No. 8,287,495 entitled "Infusion Pump System with Disposable Cartridge Having Pressure Venting and Pressure Feedback" by M. Michaud et al.; and U.S. patent application Ser. No. 61/655,833 entitled "Infusion Pump System with Disposable Cartridge Having Pressure Venting and Pressure Feedback" filed Jun. 5, 2012 by G. Kruse et al.

BACKGROUND

Many patients have a need for substantially continuous or real-time monitoring of levels of substances in their body fluids. For example, diabetic patients are advised to check their blood glucose level periodically to ensure that their blood glucose level is at a value that is within a safe range so as to avoid hyperglycemic and hypoglycemic conditions. Large fluctuations in blood glucose level indicate that a patient may need to take corrective action immediately to prevent a medical emergency, such as loss of consciousness. The corrective action typically involves receiving a dose of insulin or ingesting fast acting carbohydrates. To determine blood glucose level, a diabetic patient often utilizes a blood glucose meter (also referred to as a blood glucose monitor or "BGM"). The BGM provides a measured blood glucose level based on a blood sample of the patient. The blood sample is obtained by the patient or caregiver, such as by a finger stick, usually with the assistance of a lancing device. The device lances the skin of the patient, drawing out a small quantity of capillary blood that is then placed on a test strip for analysis by the BGM. To properly monitor a patient's blood glucose level, lancing may be performed by the patient or caregiver at regular time intervals that are dependent of the severity of the diabetes. Each lancing can be uncomfortable. Such discomfort motivates many patients to decrease the frequency of using this method to measure their blood glucose level, which may result in inadequate monitoring and, ultimately, improper insulin dosage. Similarly, variance in the accuracy of the test strips commonly used with BGMs can cause errors in the measured blood glucose level for a patient, which again which may ultimately result in improper insulin dosage due to reliance thereon.

A second type of glucose meter, a continuous glucose monitor (CGM), provides a substantially continuous estimated blood glucose level through a transcutaneous sensor that measures analytes, such as glucose, in the patient's interstitial fluid rather than their blood. Examples of CGMs include the Seven®, Seven® PLUS, and G4™ Platinum monitoring systems sold by Dexcom®, Inc. of San Diego, Calif. CGM systems typically consist of a transcutaneously-placed sensor, a transmitter, and a monitor (either a stand-alone monitor or one built into an insulin pump). Such systems and definitions of related terms are described in greater detail in, e.g.: U.S. Pat. Nos. 8,311,749; 7,711,402; and 7,497,827; each of which is hereby incorporated by reference in its entirety. A CGM system allows a patient or caregiver insert a single sensor probe under the skin for multiple days, such as for a week. Thus, the patient is only required to perform a single moderately invasive action with a single entry point in the subdermal layer on, e.g., a weekly basis. Because the CGM estimates blood glucose levels from analyzing interstitial plasma or fluid rather than blood as with BGMs, however, CGMs generally are not as well-suited for accurate blood glucose monitoring. Accordingly, CGMs are most often used for identifying trends in blood glucose levels over time and for providing estimates thereof. It is necessary to calibrate the CGM sensor's measurement of a patient's interstitial fluid to an estimated blood glucose level. For example, a voltage output or current output value of the sensor that is generated from exposure to the interstitial fluid of a patient is associated with a corresponding blood glucose level of the patient. A calibration curve defines the function that generates an estimated blood glucose level (typically provided in, e.g., mg/dL or mmol/L) for a given sensor output value (typically provided in, e.g., volts, amperes, coulombs or other output values; some values are based on optical sensors). A CGM may utilize a predetermined calibration curve that is based on collected sensor output data and corresponding blood glucose levels determined for a general patient population. With some devices, the calibration curve can be adjusted for measured blood glucose levels taken for an individual patient (e.g., via a lancing device).

A CGM, such as a portable CGM, may be incorporated with other components to provide useful medical systems. One such component is a medical infusion device used for the administration of substances such as medicaments directly into the body of a patient. Ambulatory insulin pumps are a type of portable medical infusion device that administer insulin to those diagnosed with both Type I and Type II diabetes. Portable insulin pumps are effective in the treatment of diabetes and offer an alternative to multiple daily injections of insulin via an insulin syringe or an insulin pen. Portable insulin pumps also allow for continuous insulin therapy. The continuous administration of insulin may be particularly helpful in the treatment of diabetes, where a large percentage of patients depend on the delivery of a known amount of insulin at predetermined intervals. The administration of insulin for a diabetic patient is one of a few medical indications in which the patient routinely administers the medicament to themselves by a subcutaneous modality, such as via a hypodermic syringe injection. An insulin pump provides a patient with an alternative to syringe injection for safely, reliably, and comfortably administering required doses of medication at appropriate times.

Ambulatory insulin infusion pumps, such as the T:slim® pump sold by Tandem Diabetes Care, Inc. of San Diego, Calif., the Paradigm® Revel™ pump sold by Medtronic Minimed, Inc. of Northridge, Calif., and the One Touch® Ping® pump sold by Animas Corporation of West Chester, Pa., typically allow the patient or caregiver to adjust the amount of insulin delivered, by a basal rate or a bolus, based on blood glucose data obtained by a BGM or CGM. Some ambulatory insulin infusion pumps may include the capability to interface with a BGM or CGM such as, e.g., by receiving measured or estimated blood glucose levels and prompting the user to adjust the level of insulin being administered or planned for administration or, in cases of abnormally high blood glucose readings, prompting temporary cessation of insulin administration. These portable pumps may incorporate a BGM or CGM within its hardware or may communicate with dedicated BGM or CGMs via, wired or wireless data communication protocols. Such pumps may be particularly important in facilitating patient compliance and improved or more accurate treatment of the condition. Other portable pumps being developed have the ability for the automatic control of medicament delivery based on, e.g., CGM sensor data. The delivery of insulin from a portable insulin pump making use of CGM data necessitates accurate and reliable CGM output.

In a CGM system, whether of the dedicated, "standalone" system or one that is incorporated with a medical device such as a portable insulin pump, the calibration of the CGM sensor may drift over time. The drift may occur as a result of, for example, aging of the sensor and reaction of the patient's body to the sensor probe itself. Because of this drift, it is necessary to update or adjust a calibration curve after a user has inserted the CGM sensor probe to obtain the most accurate estimates possible. The calibration curve of a CGM system can be updated by obtaining a measured blood glucose level, such as via a BGM that utilizes a sample of a patient's blood, and entering the measured blood glucose level into the CGM. The CGM can compare its sensor output value at a particular time with the measured blood glucose level obtained at substantially the same time and adjust its calibration curve to reflect the obtained measured blood glucose level. The adjustment may utilize, for example, linear regression techniques for data analysis, to produce an adjusted calibration curve. Generally, a calibration of the CGM with a measured blood glucose level is recommended at least once every twelve hours, as the sensor drift can become relatively more significant at greater time intervals.

Sensor drift, and the need for calibration, can be more pronounced if a patient does not follow the recommended sensor change schedule. As noted, most CGM systems, whether a dedicated CGM or one that is incorporated in a medical device such as a portable insulin pump, utilize a sensor probe that is placed under the skin for a period of days, e.g., approximately seven days, after which the sensor probe is replaced with a new sensor probe. Patients may, however, leave a sensor probe in place for a longer time, to decrease the frequency of performing the insertion procedure. A sensor probe that has remained unchanged in a patient for a longer time period may experience increased output drift. In other cases, the sensor drift may occur at a higher rate early in its life, depending upon a variety of factors.

Although CGM calibration via a measured blood glucose level is useful for correcting the correlation of the CGM device sensor output to blood glucose level at the time of calibration, sensor drift can cause a sensor output reading at a time between calibrations to vary, even significantly vary, from what a measured blood glucose level would be if taken at approximately the same time. Therefore, there is a need for a CGM that can be more effectively calibrated to provide more accurate estimates of blood glucose level.

SUMMARY

Disclosed is a portable medical monitor system that generates an estimate of a level of an analyte, such as glucose, that is being monitored. The portable medical monitor system produces a calibration curve for generating the estimate of the level being monitored, wherein the calibration curve is based on at least two data values of the level being monitored. The system determines a transformation function based on the produced calibration curve and at least one preceding calibration curve such that the transformation function produces a predictive calibration curve at a desired time, or produces one or more predictive curves for future time values. The system next generates an estimated level value of the analyte being monitored, based on sensor output from a sensor associated with the portable medical monitor system, in accordance with the predictive calibration curve for the desired time value. In this way, the predictive calibration curve provides an estimate of the monitored analyte that is better than the estimate that would be produced using a past calibration curve or preceding curve. Rather, the provided estimate is a result of using data analysis techniques to generate an estimate of the level being monitored from a new, predictive calibration curve produced at a time when the estimate is desired. In the case of a monitor system for monitoring blood glucose level of a patient, the calibration curve from which blood glucose level estimates are determined is a curve that is predicted from two or more calibration curves obtained prior to the time of the desired estimate. The technique described herein provides a more accurate estimated blood glucose level for patients utilizing portable continuous glucose meters.

The portable medical monitor system can be incorporated with other components. For example, the portable medical monitor system can be incorporated with an insulin pump to provide a portable insulin infusion device. For the portable insulin infusion device, the sensor is a glucose sensor, and the technique described herein provides a more accurate estimated blood glucose level for more accurate delivery of insulin to the patient.

Other features and advantages should be apparent from the following description of preferred embodiments that illustrate, by way of example, the principles disclosed.

BRIEF DESCRIPTION OF THE DRAWINGS

The drawings illustrate embodiments of the technology and are not limiting. For clarity and ease of illustration, the drawings may not be made to scale and, in some instances, various aspects may be shown exaggerated or enlarged to facilitate an understanding of particular embodiments.

DETAILED DESCRIPTION

Figure 1:
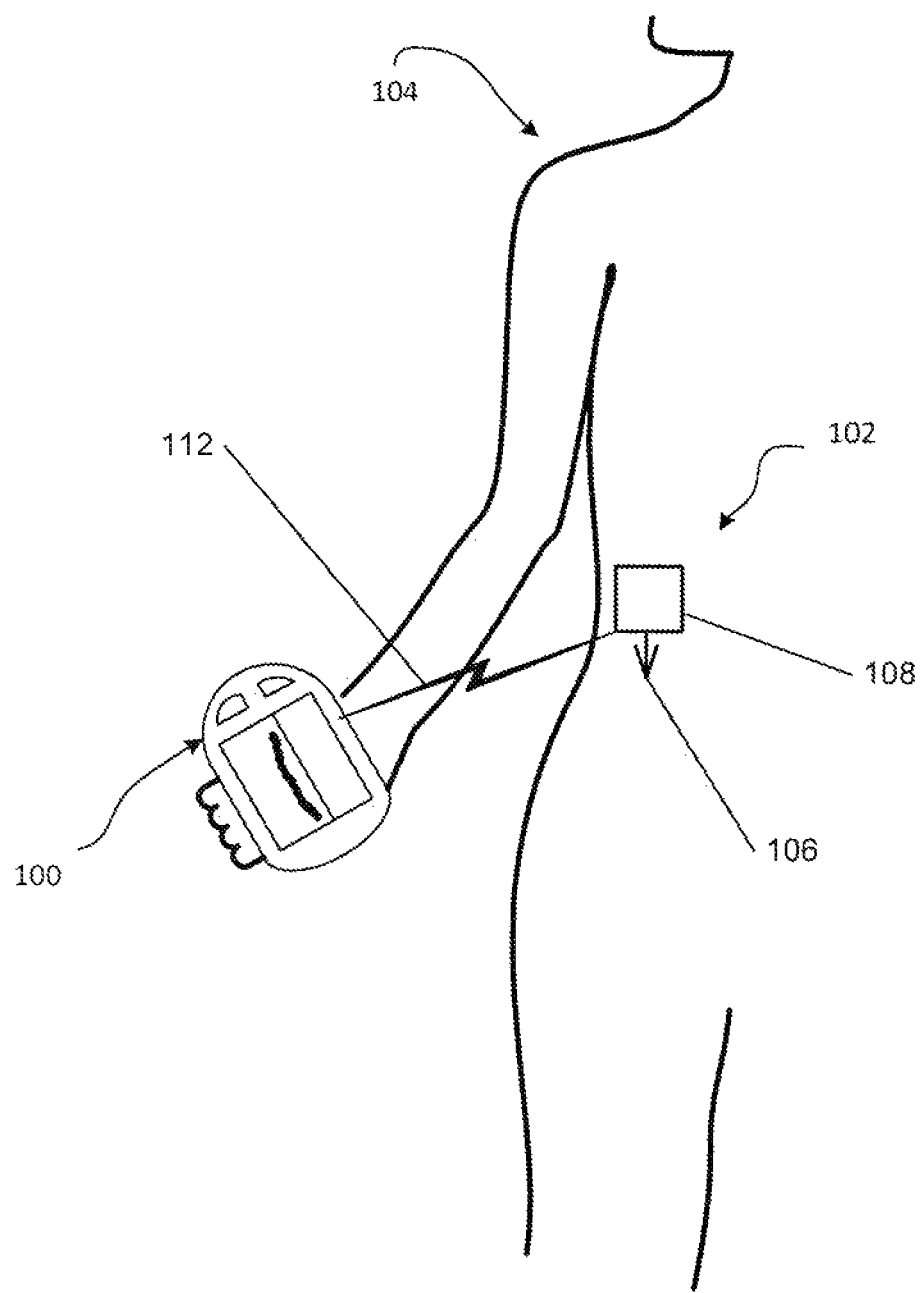
FIG. 1 illustrates an exemplary portable medical monitor system constructed in accordance with the disclosure.

FIG. 1 shows an exemplary portable medical monitor system 100. The illustrated portable medical monitor system 100 includes a portable infusion device, such as an insulin infusion pump, as well as an analyte monitor, such as a glucose monitor. A sensor 102 is affixed to a patient 104 and is associated with the infusion device. The sensor 102 includes a sensor probe 106, which is configured to be inserted to a point below the dermal layer (skin) of patient 104. The sensor probe 106, thus placed transcutaneously, is exposed to the patient's interstitial fluid or plasma and reacts with that interstitial fluid to produce a signal that can be correlated with an analyte level such as the patient's blood glucose (BG) level. The sensor 102 includes a sensor body 108 that transmits data associated with the interstitial fluid to which the sensor probe is exposed. The data may be transmitted from the sensor 102 to the blood glucose monitoring system 100 via a wireless transmitter, such as a near field communication (NFC) radio frequency (RF) transmitter or a transmitter operating according to a "WiFi" or "Bluetooth" protocol or the like, or the data may be transmitted via a wire connector from the sensor 102 to the monitor system 100. Transmission of sensor data to the blood glucose monitor system 100 by wireless or wired connection is represented in FIG. 1 by the arrow line 112.

Figure 2:
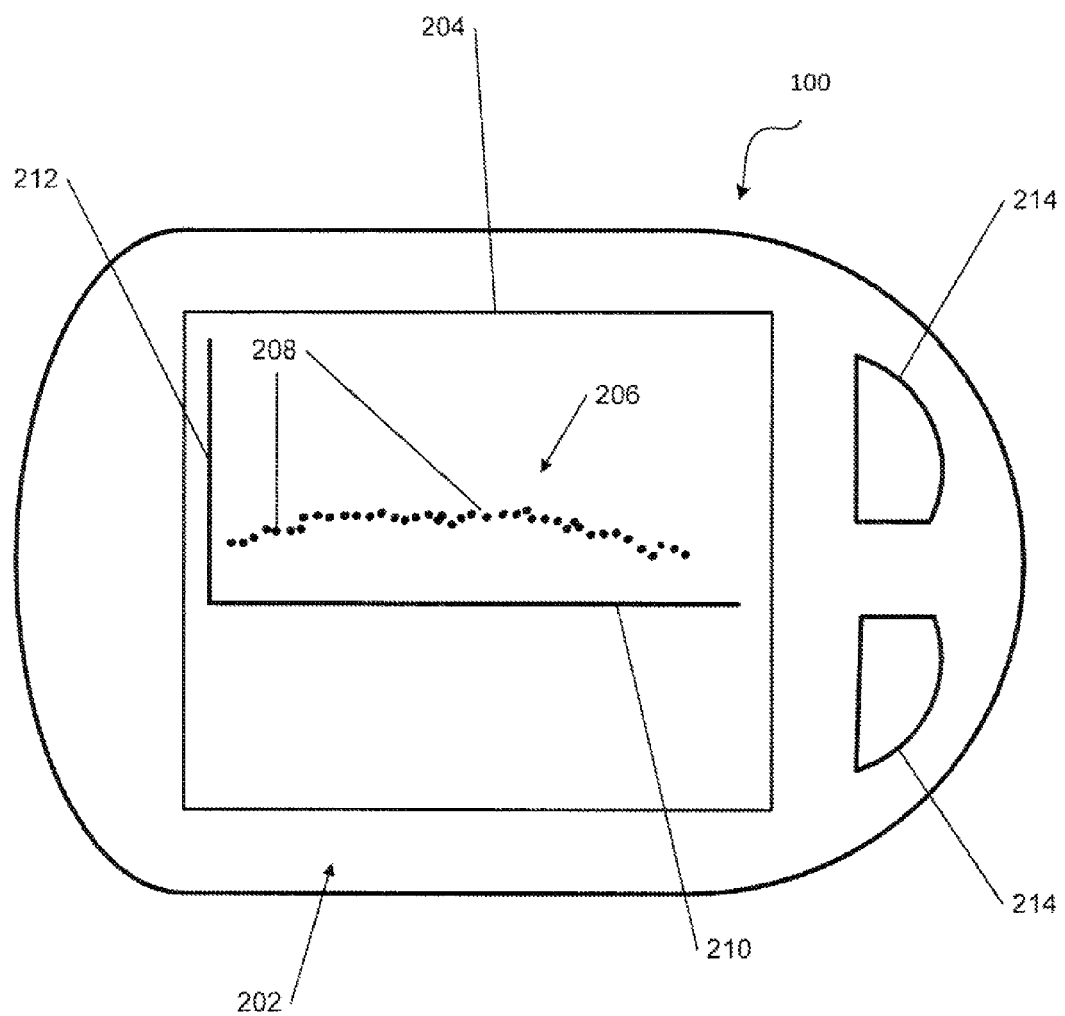
FIG. 2 shows the portable medical monitor system illustrated in FIG. 1.

FIG. 2 shows a front face 202 of the portable medical monitor system 100. The system includes a display 204 that provides a user interface for receiving user input and for showing information about operation of the system and for showing data received from the sensor 102 (FIG. 1). For example, the monitor system 100 can provide a graphical image on the display 204 to show a graph 206 of data points 208 representing estimated blood glucose data plotted as a function of time along a horizontal axis 210. The estimated blood glucose values may be represented along a vertical axis 212 in suitable units as known to those of skill in the art, such as, e.g., millimols per liter (mmol/L), milligrams per deciliter (mg/dL), etc. Each of the data points 208 represents an estimated BG level at a particular time. The data points 208 may represent an actual measured BG level derived from a direct analysis of the patient's blood obtained via a lancing device, or as described above the data points may represent estimated BG level from the patient's interstitial fluid via the subcutaneously-placed sensor 102 (FIG. 1). The displayed data also may represent both types of actual and estimated blood glucose levels in any number of combined, superimposed or even animated formats. Any number of useful graphical and/or alphanumeric images may be shown at various times on the display 204. The system 100 may include input buttons 214 for receiving user inputs for control of the system, with inputs such as up/down, yes/no, on/off, etc. Alternatively, or in addition to the input buttons, the display 204 may be provided as a touchscreen so that the displayed image may show symbols or icons that the user may touch to indicate a desired input. A microphone (not shown) may also be present for receiving audio input. Other input formats together or in combination with those disclosed herein as known in the art may be included in the system 100.

Figure 3:
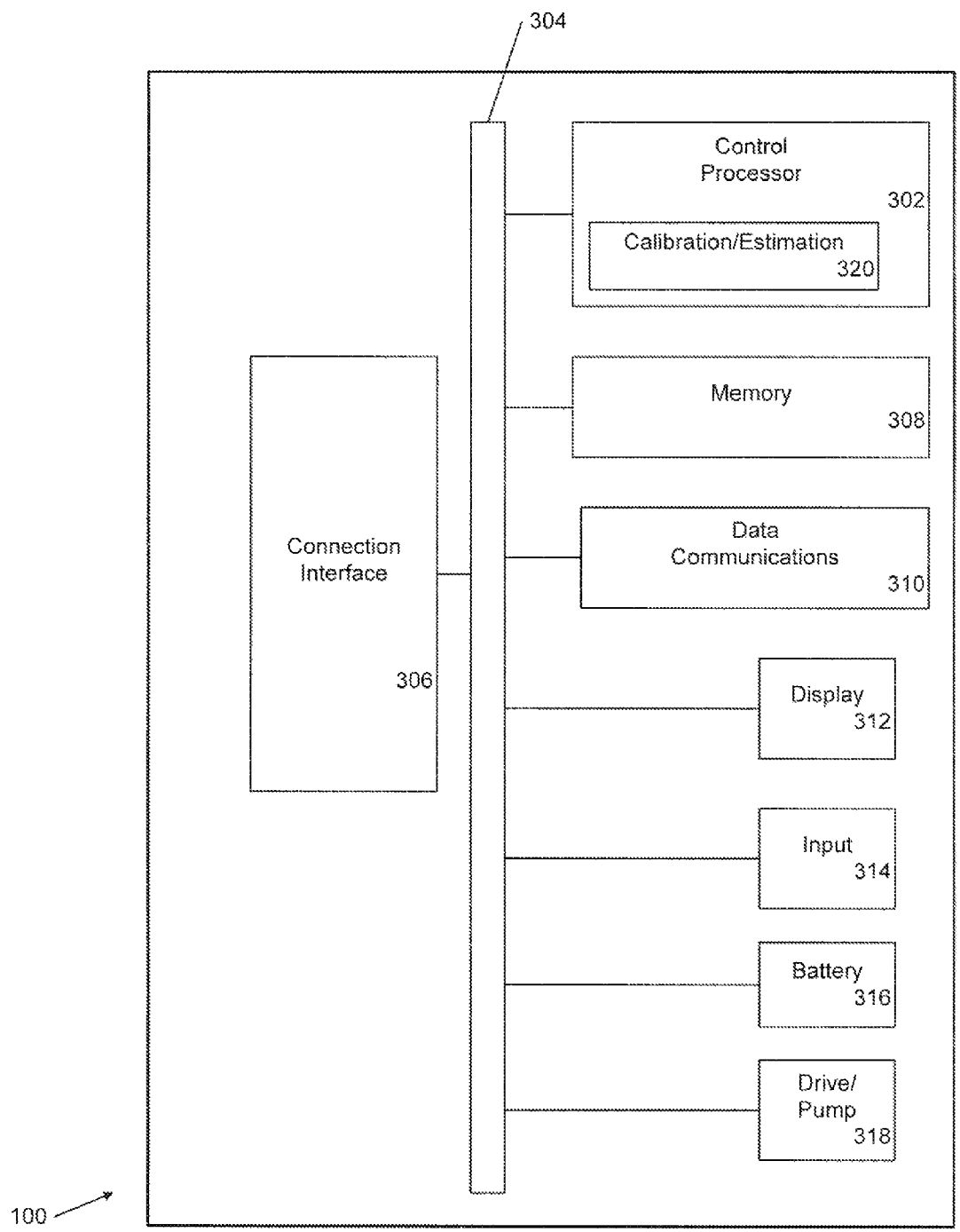
FIG. 3 is a block diagram of the components within the portable medical monitor device of FIG. 1.

FIG. 3 is a block diagram of components within the portable medical monitor system 100. A control processor 302 receives data from other components of the system 100 over a system bus 304. As described further below, at a time when an estimate is desired, the control processor calculates estimates of patient BG level as a function of the sensor output. This is accomplished by generating a data calibration curve based on, e.g., at least two measured (obtained, e.g., by a finger stick) BG levels of the patient and determining a transformation function based on the data calibration curve and at least one preceding calibration curve such that the transformation function produces at least one predictive calibration curve, comprising a predictive calibration curve at a desired time, or one or more predictive curves for future time values. Alternatively to using at least two measured values, the estimate may be calculated using at least one measured BG level and at least one other data value such as a default or derived value, with generating a calibration curve based on the data values and determining a transformation function and producing at least one predictive calibration curve. The control processor 302 generates an estimated BG level corresponding to a sensor output value of the sensor 102 in accordance with the predictive calibration curve.

A connection interface 306 of the monitor system 100 provides a physical connection to external devices, and may comprise, for example, a connector port such as a Universal Serial Bus (USB) port, an "Ethernet" connection, or other wired communication connection between the BG monitor system 100 and the external device such as sensor 102 (FIG. 1). The system 100 may receive electrical power as well as data transmitted via the connection interface 306.

The control processor 302 controls operation of the various elements of the portable medical monitor system 100 that are connected to the system bus 304. The control processor operates according to program instructions that may be stored in system memory 308. Program instructions may also be stored in processor memory that is incorporated in the control processor 302. The control processor also stores data, including operational data and device parameters, in the system memory 308. The control processor controls a data communications element 310 that may comprise a receiver/transmitter for wireless RF communications, such as "WiFi" communications or "Bluetooth" communications between the portable monitor system 100 and compatible external systems and networks, including the sensor 102 (FIG. 1). The system 100 includes a display element 312 such as a graphical liquid crystal display (LCD) or the like, or such as a touch screen display, which is capable of displaying output and receiving user input. The system may include an input mechanism 314 such as a keypad or buttons or switches for receiving user input and for controlling on/off operation of the system. The monitor system 100 is powered by a battery 316, which may be recharged with electrical power received via an electrical connection through the connection interface 306. As noted above, the system 100 comprises an insulin pump device, and therefore the system also includes a drive/pump element 318 such as a pumping mechanism for delivery of insulin fluid to the patient.

The system 100 receives sensor output from the physical connection interface 306 or from the wireless data communications element 310. The sensor output can comprise output from traditional physical sensors that monitor a patient level such as body temperature, blood pressure, and the like, or they can be chemical or biological sensors which utilize chemical or biological reactions to detect and quantify a specific level of analyte, such as glucose, or to detect and/or quantify the occurrence of an event. In the illustrated embodiment, the analyte being monitored is glucose. An exemplary and well-known chemical or biosensor is an enzyme electrode for the detection of glucose. The glucose level sensor 102 may comprise such a sensor. Glucose level sensors typically include a bioactive surface of immobilized glucose oxidase sandwiched between a polycarbonate and cellulose acetate membrane. The sensor typically comprises a platinum electrode and the output is typically a low voltage or a low current on the order of nanoamperes. For example, the electrical voltage or current output of the sensor may correspond to an estimated blood glucose level. Myriad chemical and biological sensors are available and are well known in the art, such as pH sensors for in vive blood gases, fiber-optic glucose sensors, biosensors based on transition metal hexcyanoferrates, and chemically prepared grapheme-based nanomaterials.

The memory 308 of the system 100 may be any type of memory capable of storing data and retrieving that data for transfer to one or more other components of the device, such as the control processor 302. The memory may comprise one or more of a Flash memory, SRAM, ROM, DRAM, RAM, EPROM, dynamic storage, and the like. For the illustrated portable infusion pump device 100 of FIG. 1, the memory 308 may be coupled to the control processor 302 and may be configured to receive and store one or more device parameters comprising: user input data from the touch screen, user input from buttons or switches, time, date, external sensor readings, device operating status, device messages to the user, user templates or predetermined fluid delivery patterns. The device parameters may be stored as a discrete data set at a particular point in time, a multitude of sequential discrete data sets separated by a period of time, or what is effectively termed "real-time" or continuous recording of the device parameters as fast as the system will allow. Other methods of recording device parameters such as initiating a recording based upon a trigger event are readily apparent and well known to those of skill in the art.

The memory 308 can also be configured to store one or more personalized (e.g., user-defined) delivery profiles, such as a profile based on a user's selection and/or grouping of various input parameters; past generated delivery profiles; recommended delivery profiles; one or more traditional delivery profiles (e.g., square wave, dual square wave, basal and bolus rate profiles); and/or the like. The memory can also store other device parameters such as user information, history of use, glucose measurements, compliance, an accessible calendar of events, and the like. An infusion workflow, or protocol, may be at least part of a program that displays a sequence of menu pages to assist a user to at least program or control the portable infusion device and/or at least one operation comprising input, change, confirm, or view various information within the device. Any part of a workflow or protocol may include any number of queries for prompting the user to enter, modify, or confirm information, which are typically presented to the user on the display 312.

The monitor system 100 includes a calibration/estimation component 320 that generates calibration curves and also produces BG level estimates according to the calibration curves, in response to an output signal from the associated sensor. In some embodiments, the sensor probe, which typically but not necessarily is located beneath the skin of the patient, reacts with the patient's interstitial fluid and produces a sensor output signal characterized by a voltage and current. Other sensor configurations may be utilized, with different constructions and different measurement protocols. The calibration/estimation block 320 of the system 100 receives the sensor output signal and in response produces an estimate of patient BG level. The calibration/estimation component is illustrated in FIG. 3 as a component of the control processor 302, to indicate that the calibration/estimation component is provided as an application comprising program instructions that are stored in the memory 308 and that are executed by the control processor 302 to perform the functions of generating calibration curves and producing glucose level estimates. The calibration/estimation block 320, however, may be provided as an independent module that is activated by the control processor to perform the respective calibration and estimation functions, or the block 320 may be provided as a plurality of modules the collectively perform the calibration and estimation functions. In such circumstances, the calibration/estimation component may directly communicate over the system bus 304 with the control processor and other components.

Figure 4:
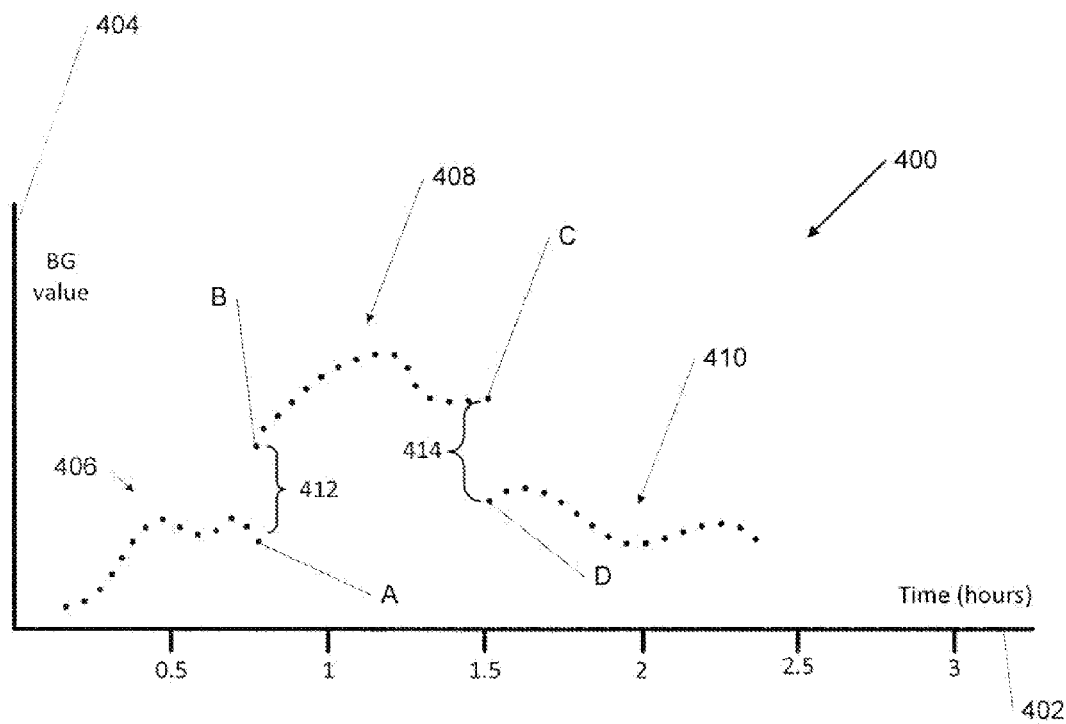
FIG. 4 is a graphical depiction of conventional glucose meter output with calibration correction due to received measured blood glucose data.

FIG. 4 is a graphical depiction of conventional glucose meter output 400, with calibration correction, based upon received measured BG data as a function of time (hours) on the horizontal axis 402. Estimated glucose level in mg/dL or mmol/L is represented on the vertical axis 404. A first portion 406 of the output 400 shows the estimated BG level produced by the conventional system as it varies over time, based on sensor output of the conventional system. That is, a particular (voltage/current, etc.) output of the sensor is initially calibrated to produce a corresponding BG level over time using a calibration curve (not shown). A second portion 408 of the output 400 shows the estimated BG level produced by the conventional system as it varies over time, based on sensor output of the conventional system. A third portion 410 of the output 400 shows the estimated BG level produced by the conventional system as it varies over time, based on sensor output of the conventional system.

In the example of FIG. 4, at a time of approximately 0.8 hours after the start of the first portion 406, the conventional system receives a measured BG level in the form of a BG reading, such as obtained from a finger stick. At that time, the conventional system, whose output is depicted in FIG. 4, determines an error in the form of a difference between a data point representing estimated BG level (the pair of sensor output and corresponding estimated BG level), and a data point representing the actual, measured, BG level. That is, the then-existing calibration curve relied upon at time t=0.8 hours indicated that the sensor output level corresponded to a glucose level of "A" mmol/L. The actual BG level obtained from a finger stick at t=0.8 hours indicated that the glucose level was "B" mmol/L. With the conventional system, the new BG reading "B" can be used to produce a new calibration curve, having one end point at "B". This discrepancy between estimate "A" and measured "B" is reflected in the discontinuity, or vertical change, indicated by the brackets 412 of the estimated BG level at the time the actual measured BG value is received. The conventional system in response typically adjusts its calibration curve (not shown) to compensate for the discrepancy based on these data. Thereafter, the conventional system uses this newly-adjusted calibration curve having "B" at one end point to estimate blood glucose levels over time based on its sensor data, as shown in a second portion 408 of the output graph 400, until the next actual BG data value is received at approximately time t=1.5 hours, whereupon the conventional system again adjusts its calibration curve using the same technique. That is, the then-existing calibration curve relied upon at time t=1.5 hours indicated that the sensor output level corresponded to a glucose level of "C" mmol/L, but the actual BG level obtained from a finger stick at t=1.5 hours indicated that the estimated glucose level should more accurately correspond to a glucose level of "D" mmol/L. This discrepancy is reflected in the discontinuity, or vertical change, indicated by the brackets 414 of the estimated BG level at the time the actual measured BG value is received. This comparison of actual BG data to a previously-calculated calibration curve to form the basis of an adjusted calibration curve is repeated through the useful life of such a conventional CGM system.

Figure 5:
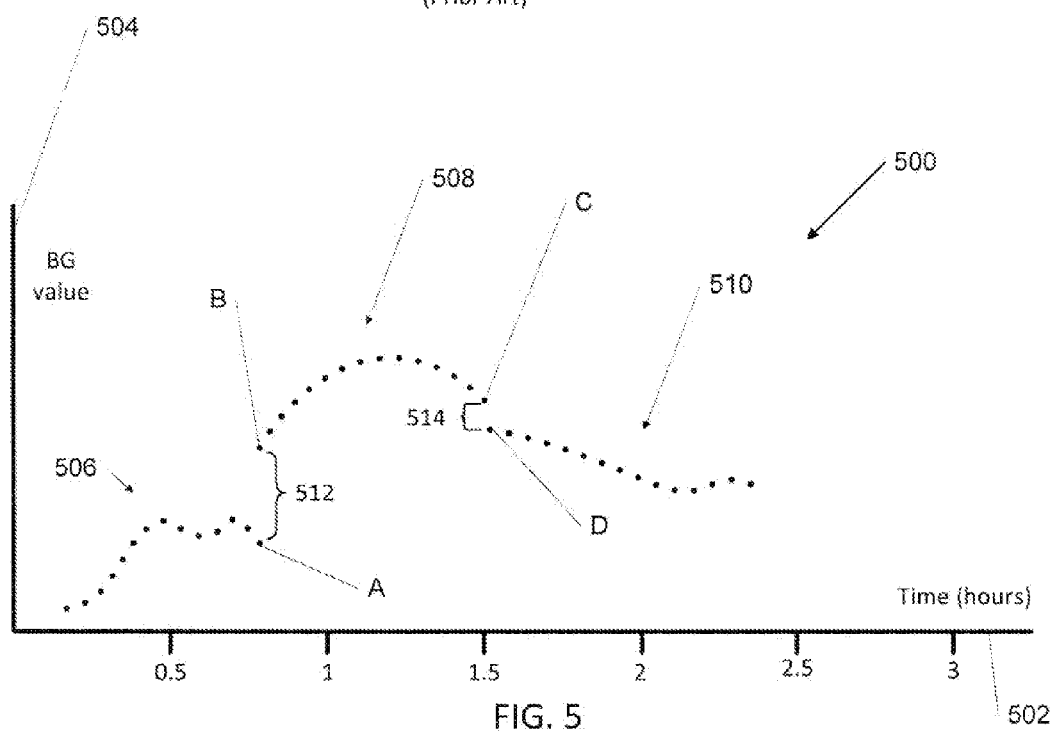
FIG. 5 is a graphical depiction of glucose meter output using predictive calibration as disclosed herein.

FIG. 5 is a graphical depiction of glucose meter output 500 using predictive calibration as disclosed herein. In FIG. 5, time in hours is again represented on the horizontal axis 502 and estimated glucose level in mg/dL or millimol/Liter (mmol/L) is again represented on the vertical axis 504. The graph 500 is generated according to a particular voltage/current output of the sensor that is associated with the monitor system and is calibrated to produce a corresponding BG level. However, the calibration is achieved using the inventive predictive calibration disclosed herein and as described further below. The output curve 500 at a first portion 506 generally follows the curve of the conventional system depicted in FIG. 4. A second portion 508 of the estimated glucose level output is produced using the inventive predictive calibration disclosed herein and as described further below. A third portion 510 of the estimated glucose level output is produced using the inventive predictive calibration disclosed herein and as described further below. The predictive calibration technique disclosed herein utilizes the first curve 506 as a preceding calibration curve and after the time t=0.8 hours incorporates additional BG levels to generate the next curve 508. As illustrated in FIG. 5, the predictive calibration disclosed herein provides estimates of BG level that are more accurate over time, as evidenced by the reduced error when the actual BG level is obtained from a finger stick at approximately the time t=1.5 hours. The graph of system output 500 in FIG. 5 is notable in part in that discontinuities of conventional systems, such as the drops in FIG. 4 at times 512, 514 as compared with the drops 412 and 414 depicted in FIG. 4. The drops or discontinuities 512, 514 are comparatively less pronounced for systems using predictive calibration.

Figure 6:
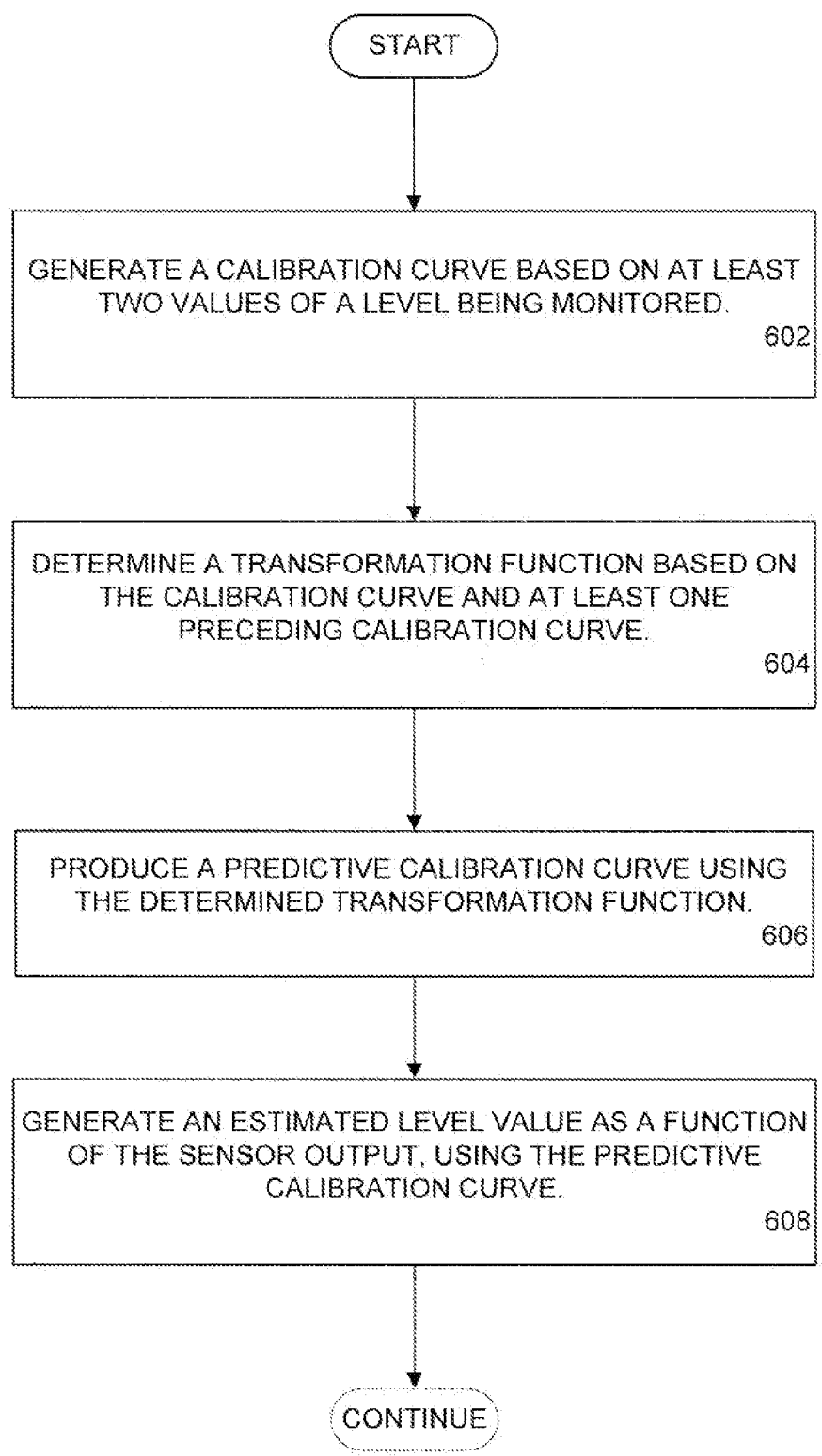
FIG. 6 is a flow diagram that illustrates the predictive calibration operation of the system illustrated in FIG. 1.

FIG. 6 is a flow diagram that illustrates the operations performed by the control processor of the monitor system when executing program instructions to provide estimates of glucose level using the predictive calibration technique disclosed herein. In the first operation of the disclosed predictive calibration technique, indicated by the flow diagram block numbered 602, the control processor of the monitor system generates a calibration curve based on data values, such as output values from the sensor that is associated with the monitor system. The calibration curve is generated using at least two data points, each of which pairs a voltage/current output value from the sensor with a corresponding measured blood glucose level. For example, the calibration curve may be generated using the two most recent actual measured BG level readings obtained by the patient with a finger stick procedure. If desired, the data calibration curve may be generated using more than two measured BG level data points. The graphs illustrated in FIG. 7 and FIG. 8 illustrate calibration curves using linear and non-linear techniques, respectively.

Figure 7:
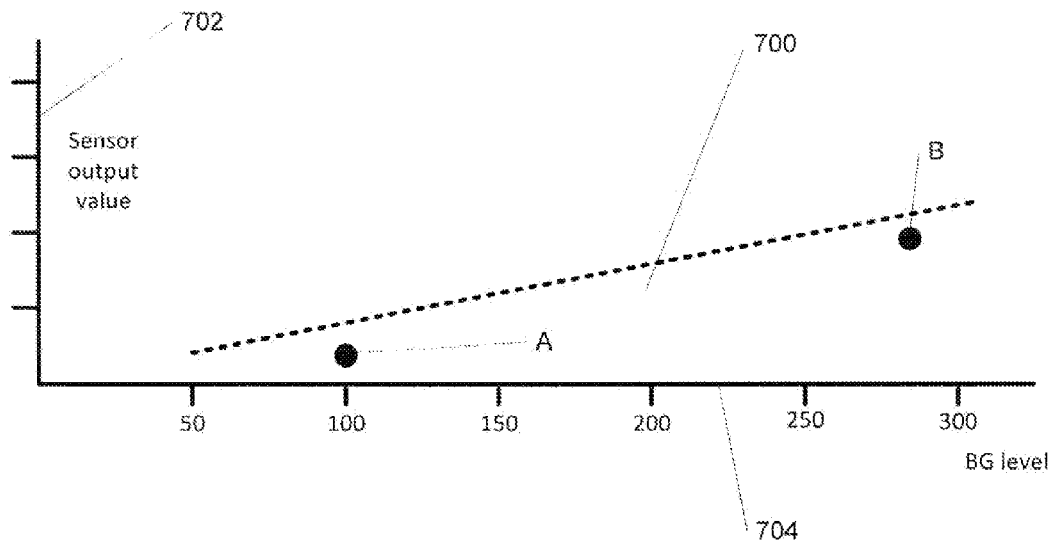
FIG. 7 is an example of a current calibration curve used in the system of FIG. 1.
Figure 8:
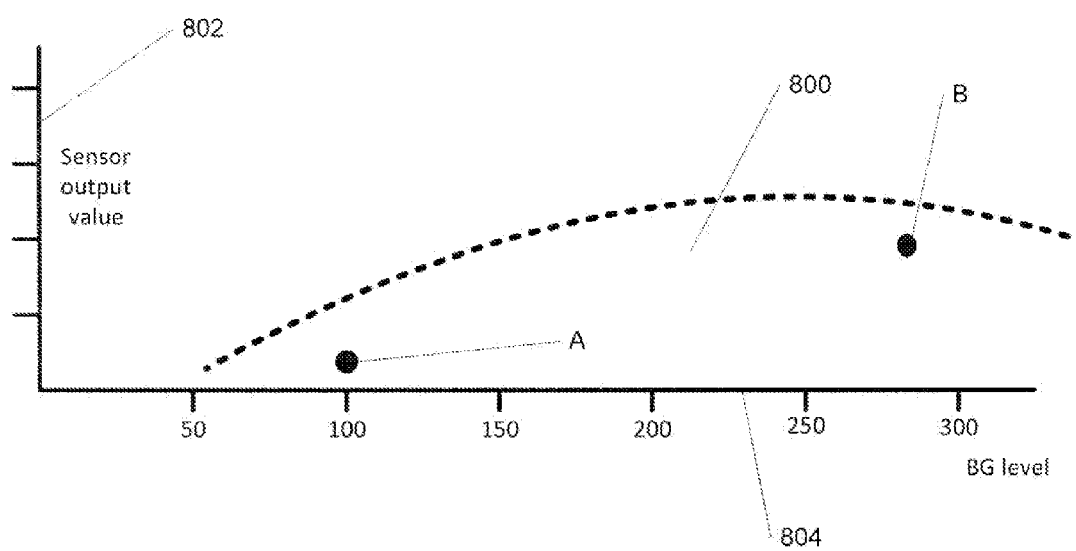
FIG. 8 is an example of a current calibration curve used in the system of FIG. 1.

FIG. 7 is an example of a linear calibration curve that may comprise the calibration curve referred to in the discussion of FIG. 6 using two data points. The calibration curve 700 of FIG. 7 is shown as a dashed line and provides a function (i.e., a calibration "curve") such that the control processor responds to a sensor output value along the vertical axis 702 with a corresponding estimated BG level along the horizontal axis 704 that is produced as output BG level in mg/dL (or mmol/L). The sensor output value may be specified, for example, in units of volts or amperes, or may be expressed as a percentage of full sensor output from zero percent to one hundred percent; other suitable functions of sensor output may be used. The calibrated sensor output, provided as estimated BG level, is typically specified in units of milligrams/deciliter (mg/dL) or in units of millimol/Liter (mmol/L).

FIG. 7 shows two measured BG level readings, obtained by the patient from a finger stick procedure, that are indicated as points "A" and "B" in the FIG. 7 graph. That is, the curve 700 reflects a linear relationship between the data values from which it is produced, which determine the straight line (linear) function that makes up or comprises the calibration curve. In FIG. 7, the measured values A and B do not themselves lie on the calibration curve itself, as is not unusual for data estimation such as calibration. Moreover, the calibration curve 700 is based in part on preceding data values (see FIG. 9), as described further below. The preceding data values contribute to the shape of the calibration curve 700. Alternatively, the system may be configured to use only the measured readings A and B so they appear on the curve 700. In addition, the system may be configured so the values A and B are not both measured values. That is, one or more of the values from which the calibration curve is determined may be default, determined, derived, or calculated values. For any value of the sensor output on the vertical axis 702, the calibration curve 700 provides a corresponding estimated BG level along the horizontal axis 704 that is produced as the output of the control processor (FIG. 3).

In FIG. 7, measured BG data points may be used to generate the calibration curve 700, if desired. As noted, the calibration curve 700 shows a linear relationship based on the two BG data points A and B. Thus, if more than two BG data points are used, linear regression techniques may be used to generate a corresponding linear calibration function based on the more-than-two BG data points. The calibration curve may or may not pass through the origin (0, 0), in accordance with knowledge of which alternative provides a better fit between sensor output and measured BG data. A linear calibration curve is a relatively simple function to implement, and is generally accepted for providing accurate calibration between sensor output levels and estimated BG levels. The monitor system, however, may be configured to accommodate non-linear models rather than linear models, or to accommodate both. For example, the control processor may be configured to utilize both linear and non-linear regression models, track the error values over time, and select between the two alternative models according to best error outcome as between the models. More than one non-linear regression model may be utilized.

FIG. 8 shows an exemplary calibration curve 800 that represents a non-linear, polynomial regression applied to the BG readings "A" and "B" first shown in FIG. 7. In FIG. 8, sensor output values are indicated along the vertical axis 802 and corresponding estimated BG levels are indicated along the horizontal axis 804. FIG. 8 shows the same two BG data points A and B as shown in FIG. 7, but unlike the linear function of FIG. 7, a polynomial function is provided in FIG. 8. The choice between linear calibration curves (FIG. 7) and non-linear calibration curves (FIG. 8) are a matter of choice, and selection between the two alternatives may be based on knowledge of the expected sensor drift over time, test data that shows sensor performance at various levels of interstitial fluid readings, and the like. As noted above, the control processor may be configured to select between the alternatives.

Returning to the flow diagram of FIG. 6, the next operation of the control processor after generating the calibration curve in block 602 is indicated by the FIG. 6 flow diagram block numbered 604. This represents the control processor determining a transformation function based on the data calibration curve generated in block 602 and at least one preceding calibration curve. That is, the system 100 generates multiple calibration curves during operation, and in that sense it should be understood that the calibration curve generated in block 602, such as the curve 700 illustrated in FIG. 7, is a follow-up to a preceding calibration curve obtained earlier than the calibration curve of block 602. Each calibration curve and corresponding transformation function may be generated using all preceding data values or by using a subset of the preceding values, depending on system resources and desired operation. Thus, the predictive calibration technique disclosed herein requires at least two calibration curves: a most recent calibration curve (box 602) and a preceding calibration curve. The difference between the curves illustrates the phenomenon of sensor drift. The transformation function expresses that difference.

Figure 9:
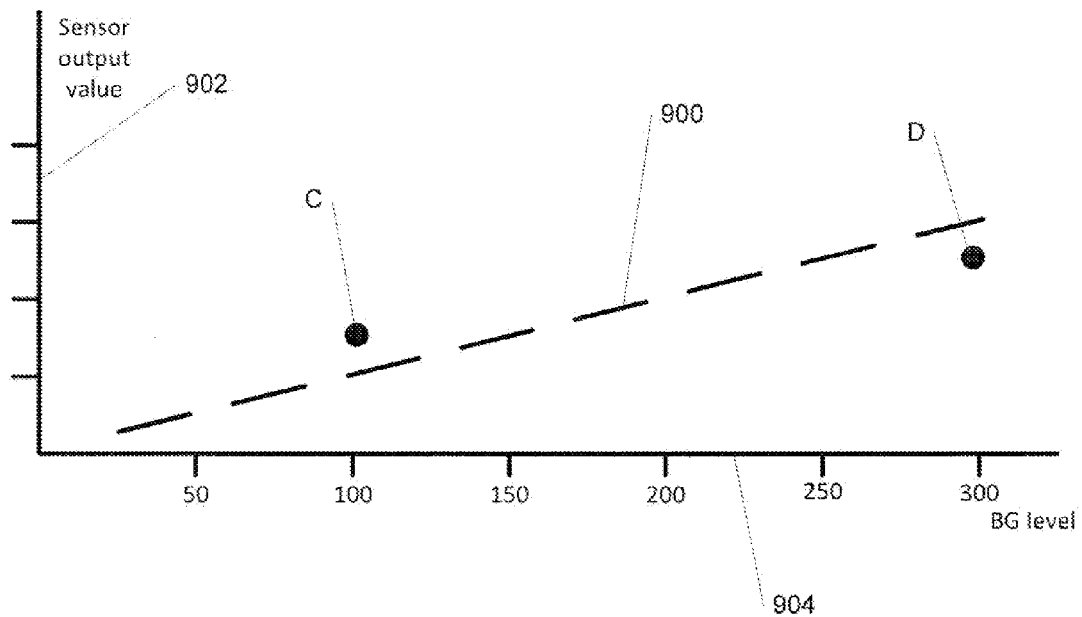
FIG. 9 shows a preceding calibration curve produced by the system of FIG. 1.
Figure 10:
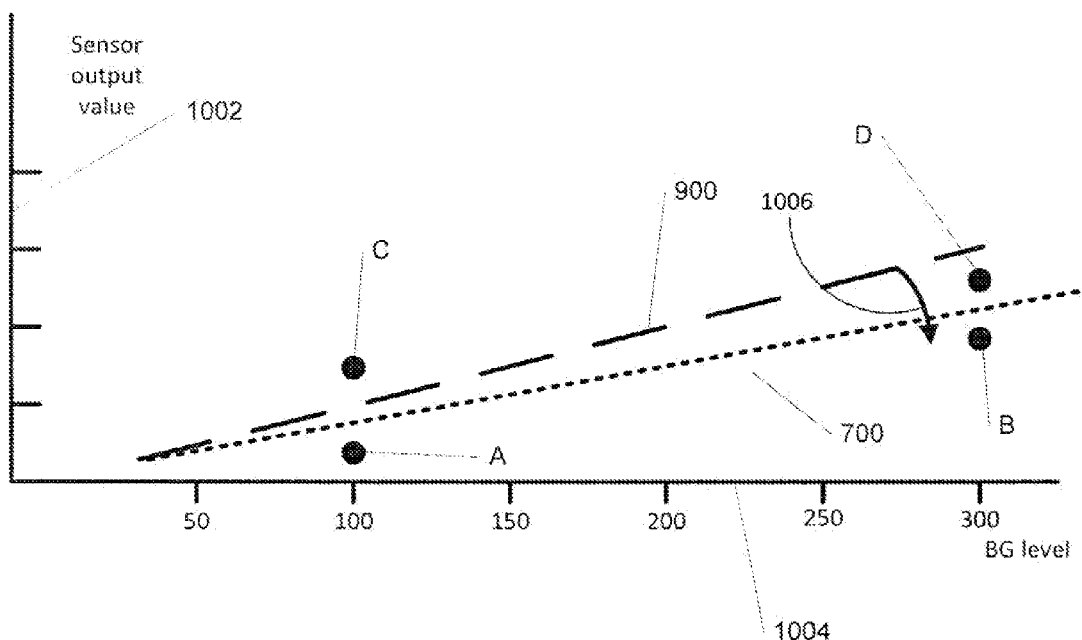
FIG. 10 shows both the current calibration curve of FIG. 7 and the preceding calibration curve of FIG. 9 on the same axes.

For example, FIG. 9 shows a preceding calibration curve 900 having a linear relationship between two BG data points called "C" and "D". It should be understood that the data points C and D of FIG. 9 were obtained earlier in time as compared to the data points A and B of FIG. 7. The vertical axis 902 shows sensor output value and the horizontal axis 904 shows the corresponding estimated BG level produced as output of the control processor and calibration/estimation component. If desired, the preceding calibration curve 900 and the FIG. 7 calibration curve 700 may be produced by all available data values or by a subset of all available data values. FIG. 10 shows both the calibration curve 700 with current data value and the preceding calibration curve 900 according to the same vertical and horizontal axes, showing sensor output value and the corresponding estimated glucose level, respectively. At the point of an initial start or first use of the monitor system and/or at the time of any fresh installation of the sensor associated with the monitor system, the preceding calibration curve 900 may be generated from default values or from historical or clinical data regarding sensor output and corresponding BG levels. As the monitor system operates over time, the control processor generates a calibration curve when a new estimated level reading is desired. The generated calibration curve is used with a preceding calibration curve, which may be the most recent preceding calibration curve, or alternatively may comprise combined values from multiple prior calibration curves and preceding data values. The technique selected, most recent preceding curve or combination of values, will depend on the values that, when used with the system, ensure a timely and more accurate predictive calibration curve. The control processor, however, may be configured to utilize all calibration curves generated during operation beginning from a system start time. The system start time may correspond to an initial configuration event, or a particular clock time, or other alternative according to desired operation. The control processor may alternatively be configured to utilize less than all the calibration curves generated during operation, such as the "n" most recently generated calibration curves, or the calibration curves generated since a particular system or clock time.

FIG. 10 shows that the calibration curve 700 may be considered as a transformation of the preceding calibration curve 900, which was generated with values C and D. That is, a transformation of the preceding calibration curve 900 provides the calibration curve 700 that is to be used in generating a current estimated value. The transformation to the calibration curve 700 from the preceding calibration curve 900 is indicated in FIG. 10 by the curved solid arrow 1006 extending from the preceding calibration curve 900 to the calibration curve 700. The solid arrow 1006 represents the sensor drift experienced by the sensor. The transformation of the preceding curve 900 to obtain the curve 700 comprises a transformation function to produce the curve 700. Although the preceding calibration curve 900 provided accurate estimated glucose level values at the time it was generated, it should be apparent that sensor drift caused that curve 900 to be inaccurate at the time of producing the calibration curve 700. Thus, at the time of producing the calibration curve 700, that curve 700 provided more accurate results than the earlier curve 900. Similarly, at any time after the calibration curve 700 was produced, there will exist a better (more accurate) curve that may be determined without additional BG data by extrapolation of the transformation implemented to get from the preceding curve 900 and to the calibration curve 700H).

Returning to the flow diagram of FIG. 6, the next operation after determining the transformation function 604 is indicated by the FIG. 6 flow diagram block numbered 606, and represents producing a predictive calibration curve using the determined transformation function. The predictive calibration curve is used to generate the estimated output level in response to the requested estimate of output level. Thus, a new predictive calibration curve is produced each time a new estimated level is calculated. That is, the new predictive calibration curve is only good for one point in time, the time when the new estimated level is desired. In many glucose monitoring systems, for example, a new blood glucose reading is generated at regular intervals, such as every five minutes of operation.

Figure 11:
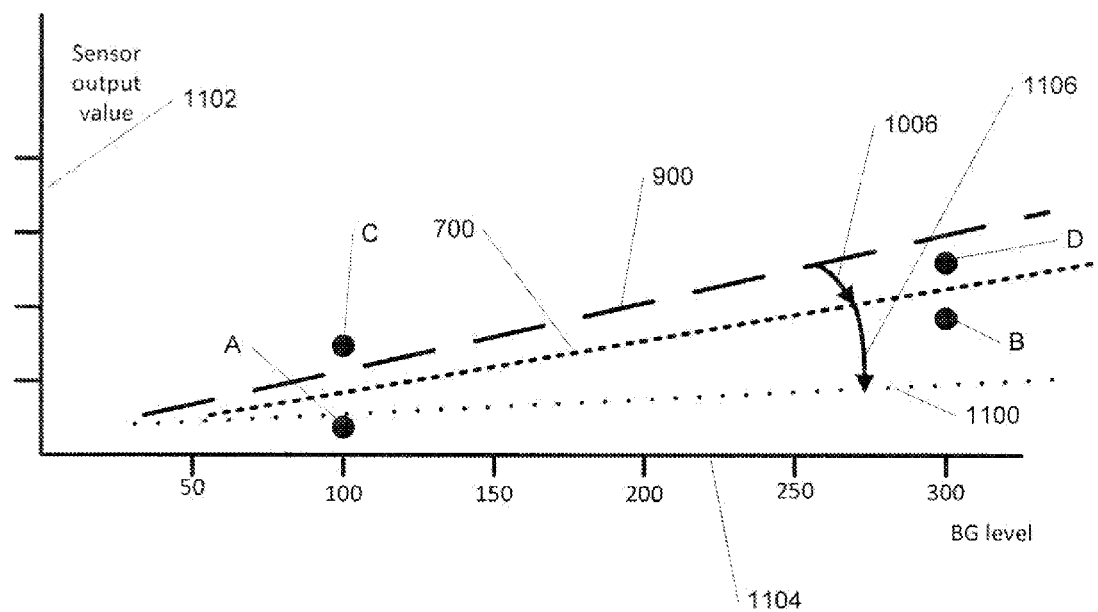
FIG. 11 shows the predictive calibration curve produced by the system of FIG. 1.

FIG. 11 illustrates the processing of the block 606 to produce a predictive calibration curve 1100. That is, given any two calibration curves, such as the calibration curve 700 and the preceding calibration curve 900, the system at block 604 determines the transformation function that expresses the difference between the calibration curve and the preceding calibration curve and in block 606 extrapolates that difference to produce a predicted calibration curve. Thus, although the prior calibration curves may be generated based on previous BG levels, the predictive calibration curve is prospective in nature. In FIG. 11, the predictive calibration curve 1100 is produced as an extrapolation of the transformation from the preceding calibration curve 900 to the calibration curve 700, both of which are illustrated in FIG. 11. That is, the predictive calibration curve 1100 is a prediction of where the proper calibration should be for a time subsequent to the time of collecting the most recent BG data point. The vertical axis 1102 shows sensor output value and the horizontal axis 1104 shows the corresponding BG level produced as output of the control processor and calibration/estimation component.

FIG. 11 shows that the transformation function is repeated in generating the predictive calibration curve 1100, except that in FIG. 11 the transformation function that is applied by the control processor is performed on the calibration curve 700, as indicated by the second transformation arrow 1106. Those skilled in the art will understand mathematical analysis techniques used for determining the transformation function required to produce one data curve from another (i.e., to produce the calibration curve 700 given the preceding calibration curve 900), and will understand techniques for applying the same transformation function to the calibration curve 700 to produce the predictive calibration curve 1100.

Returning to the flow diagram of FIG. 6, the next operation after producing the predictive calibration curve is indicated by the FIG. 6 flow diagram block numbered 608, and represents the step of generating an estimated monitored analyte level, such as glucose, using the predictive calibration curve 1100 (FIG. 11). That is, the system 100 monitors the measured BG level of a patient and uses the predictive calibration curve to generate an estimated BG level corresponding to the sensor output value. Thus, at block 608, the control processor receives a sensor output from the sensor, uses the sensor output with the predictive calibration curve 1100, and produces a corresponding estimated BG level for output to the display 204 (FIG. 2) of the system 100. The estimated BG level may also be used in initiating delivery of insulin from the system 100 to the patient 104 (FIG. 1).

As noted above, at a time when the patient next obtains a measured BG level, such as at time t=1.5 hours in FIGS. 4 and 5, the control processor 302 (FIG. 3) generates a calibration curve, based on at least two BG levels, as indicated at block 602 (FIG. 6). A preceding calibration curve, which likewise is based on at least two BG levels, is compared with the most recently-generated calibration curve, and the control processor determines a transformation function. The transformation function and the elapsed time since the transformation function was determined, when applied to the preceding calibration curve, generates the calibration curve. This processing is represented by the block 604. The transformation function and the elapsed time since the transformation function was determined, when applied to the current calibration curve, produces the predictive calibration curve, as represented by the block 606. With the predictive calibration curve, the control processor generates an estimated BG level in response to receiving a sensor output value from the sensor 102 (FIG. 1).

Figure 12:
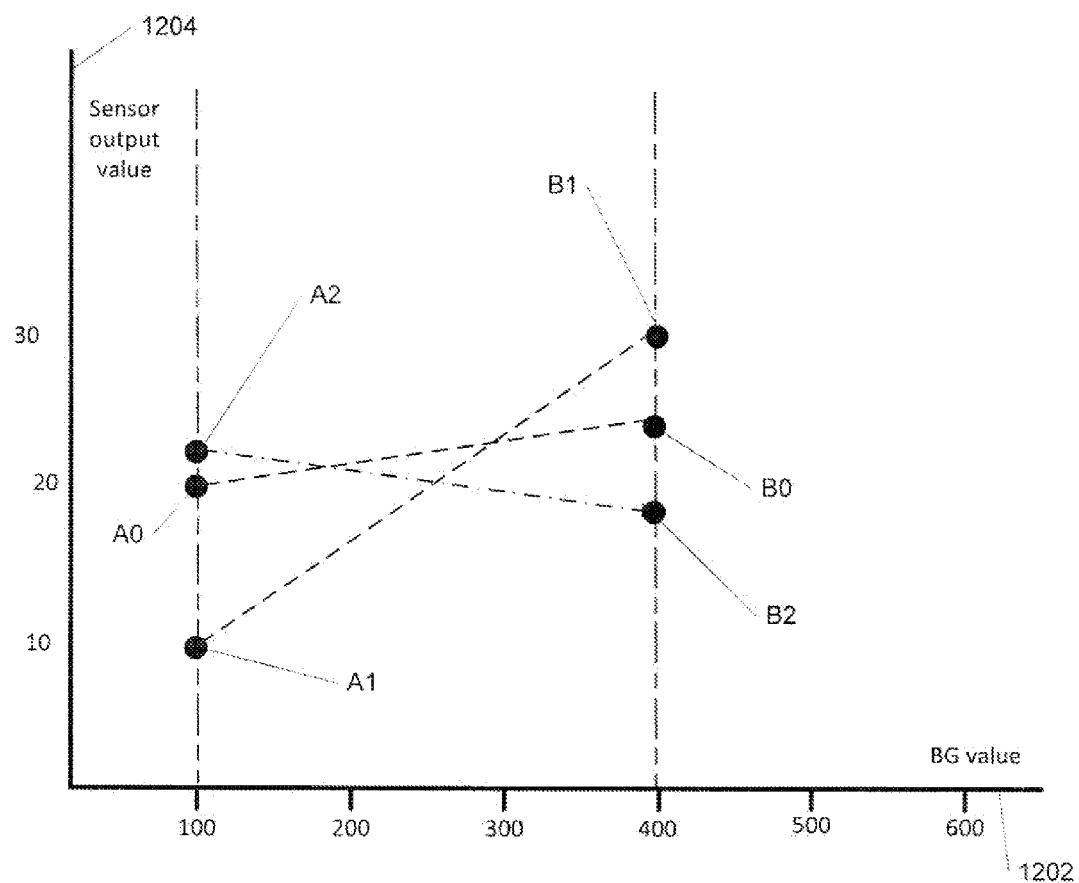
FIG. 12 is a representation of the calculation carried out by the system in determining a predictive calibration curve.

FIG. 12 is an example of the calculations carried out by the system in determining a predictive calibration curve at a time $t=t_2$ when an estimated BG level is desired from the system. FIG. 12 shows a graph of BG value on the horizontal axis 1202 and sensor output level 1204 on the vertical axis. For purposes of illustration, FIG. 12 shows a vertical dash-dot line at BG=100 and at BG=400, to establish endpoints for the curves, for purposes of explaining the example. FIG. 12 shows the curve endpoints denoted A0, A1, A2, B0, B1, and B2. FIG. 12 shows a calibration curve for a time $t=t_1$, where $t_1<t_2$, with end points of the calibration curve indicated at A1 and B1. The linear calibration curve is represented by a dashed line extending from A1 to B1, which will be denoted (A1, B1). FIG. 12 also shows a preceding calibration curve for a time $t=t_0$, where $t_0<t_1$, and with end points of the preceding calibration curve at A0 and B0. The preceding calibration curve is represented by a dashed line extending from A0 to B0, the curve denoted as (A0, B0). Both calibration curves are illustrated as linear relationships, but as noted above, estimation techniques and lines of different order may be used. Table 1 below shows an example of a transformation that provides a predictive calibration curve indicated by the end points A2 and B2 for GB levels and sensor output (SO) levels.

TABLE 1

Calibration curve A1, B1 = [BG = 100, SO = 10] and [BG = 400, SO = 30]
Preceding calibration curve A0, B0 = [BG = 100, SO = 20] and [BG = 400, SO = 22]

Table 1 shows a change for BG=100 from A0=20 to A1=10, and Table 1 shows a change for BG-=400 from B0=22 to B1=30. Using linear extrapolation, the values in Table 1 provide a transformation specified by the endpoints of A2 [BG=100, SO=20.5] and B2 [BG=400, SO=18]. These endpoints are graphed in FIG. 12 as A2 and B2, respectively. Thus, at the time $t_2$, when the estimated BG level is desired, the system generates the predictive calibration curve A2, B2 computed as noted above, and produces a BG level output for a given sensor output value, as per the predictive calibration curve from A2 to B2. The process may be repeated at a time subsequent to $t_2$, when a new predictive calibration curve will be produced and a new estimated BG level will be generated.

An example of calculations from which the predictive calibration curve of FIG. 12 can be provided may be described as follows. For the linear representation of FIG. 12, a calibration curve may be generally described by the equation $y=m_i x+b_i$ where y is the sensor output value on the vertical axis 1204 at a time $t_1$, x is the BG value on the horizontal axis 1202, $m_i$ is the slope of the ith curve, and $b_i$ is the sensor output value on the vertical axis corresponding to the BG value at time $t_i$ for the ith curve. In general, a transfer function value for a predictive calibration curve can be computed for any two preceding calibration curves at each endpoint of the predictive calibration curve, such as where BG=100 and at BG=400 in FIG. 12. The computation is based on two outputs $y_1$ and $y_2$ from each respective preceding calibration curve, using the equations above for y, and can be produced by solving as follows:

$$y_2-y_1/\Delta t=[m_2 100+b_2-m_1 100-b_1/(t_2-t_1)]$$

which simplifies to:

$$y_2-y_1/\Delta t=[(m_2-m_1)100+(b_2-b_1)]/(t_2-t_1).$$

And a similar relationship holds for a transfer function at BG=400, to establish the other endpoint of the predictive calibration curve produced as a transformation of two preceding calibration curves. Using these equations, it is possible to determine an equation for an endpoint $y_3$ on the predictive calibration curve at BG=100 at a time $t_3$, as follows:

$$y_3 = [\{[(m_2-m_1)100+(b_2-b_1)]/(t_2-t_1)\}*(t_3-t_2)]+y_2$$

at a time $t=t_3$, where $y_2$ is the value of the preceding curve at BG=100. A similar equation holds for BG=400. Using this equation above, two points on the predictive calibration curve are determined, a point at each of two (BG, SO) values, one for (100, $y_3$) and one for (400, $y_3$). If the predictive calibration curve is represented as a linear curve, as in FIG. 12, then the intercept point on the SO axis and the slope of the line can be determined using well-known techniques, which as noted above provides endpoint coordinates for the predictive calibration curve of:

$$A2[BG=100, SO=20.5] \text{ and } B2[BG=400, SO=18].$$

If more than two endpoints are used in determining the transfer function, then other techniques may also be used, also well-known in the art.

Figure 13:
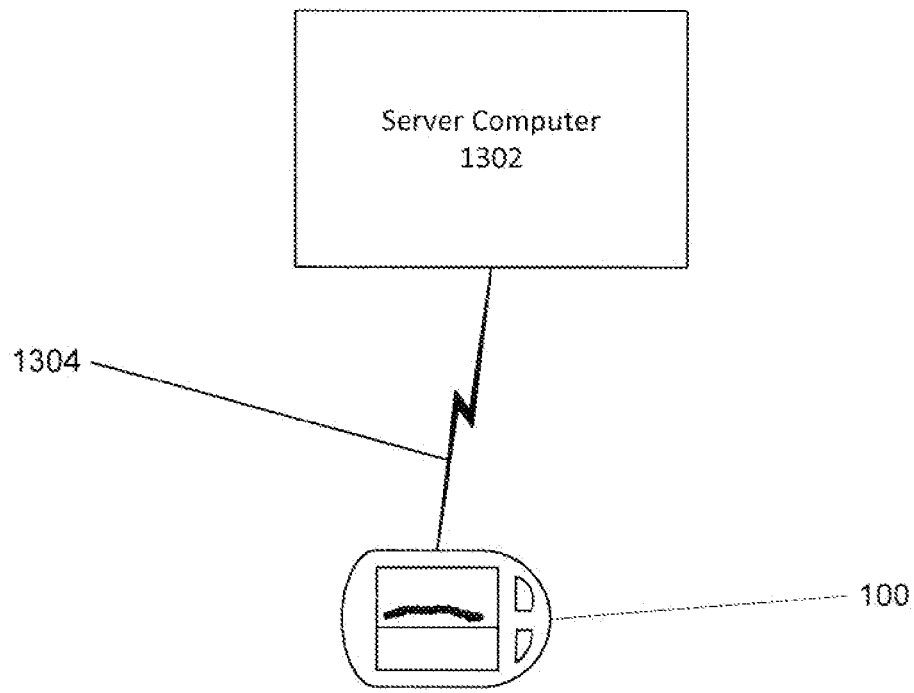
FIG. 13 is a schematic representation of network communications between the system of FIG. 1 and a server computer.

FIG. 13 shows that the portable medical monitor system 100 can be configured by a server computer 1302. The configuration, for example, may be for the purpose of updating configuration information or for installing program instructions to be executed by the control processor of the monitor system 100 to provide the functionality disclosed herein. The configuration comprises establishing a network communication link at the server computer 1302 to the portable medical monitor system 100. As noted above, the monitor system 100 may include a connection interface 306 and data communications 310 (FIG. 3) through which the monitor system may communicate over a network with external systems such as the server computer 1302, which is equipped with similar components for network communication. The network communication link between the server computer 1302 and the monitor system 100, and the transmitting of information between the two, by wireless or wired connection, is represented in FIG. 13 by the arrow line 1304. The information transmitted between the server computer 1302 and the monitor system 100 may comprise program instructions transmitted over the network communication link 1304, wherein the transmitted program instructions are configured to be stored in memory of the portable medical monitor system and executed to provide the functionality and operation of the monitor system as disclosed herein.

Although the aforementioned description specifically describes a portable medical system comprising an insulin pump for administering insulin to a patient, it should be understood that such a device is only one embodiment. A system constructed in accordance with the disclosure herein may also include any portable device having a processor that is capable of receiving output from an associated sensor and performing data analysis to generate the disclosed calibration curves and produce the estimated analyte level values.

The methods, systems, and devices discussed above are intended merely to be examples. Various embodiments may omit, substitute, or add various procedures or components as appropriate. For example, it should be appreciated that, in alternative embodiments, the methods may be performed in an order different from that described, and various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in this description to provide a thorough understanding of the embodiments. Nevertheless, it will be understood by one of ordinary skill in the art that the embodiments may be practiced without these specific details. For example, well-known circuits, processes, algorithms, structures, and techniques have been shown without unnecessary detail in order to avoid obscuring the embodiments. Further, the headings provided herein are intended merely to aid in the clarity of the descriptions of various embodiments, and should not be construed as limiting the scope of the invention or the functionality of any part of the invention. For example, certain methods or components may be implemented as part of other methods or components, even though they are described under different headings.

It is noted that embodiments may have been described as a process that is depicted as a flow diagram or block diagram. Although each diagram may describe the process as a sequential series of operations, many of the operations can be performed in parallel or concurrently. In addition, the order of the operations may be rearranged. A process may have additional steps not included in the figures. Each operation of a process is performed or executed by the processor of the device.

The description above has been provided in terms of presently preferred embodiments so that an understanding of the present invention can be conveyed. There are, however, many configurations and techniques for data management systems that were not specifically described herein, but with which the present invention is applicable. The present invention should therefore not be seen as limited to the particular embodiments described herein, but rather, it should be understood that the present invention has wide applicability with respect to data management generally. All modifications, variations, or equivalent arrangements and implementations that are within the scope of the attached claims should therefore be considered within the scope of the invention.

What is claimed is:

1. A method of operating a portable medical monitor system that generates an estimate of an analyte level of a patient being monitored with an analyte sensor, the method comprising:
   generating a current calibration curve for generating the estimate of the analyte level being monitored, wherein the current calibration curve is based on at least two measured data values of the level being monitored;
   determining a transformation function based on the current calibration curve and at least one preceding calibration curve such that the transformation function produces a predictive calibration curve that predicts changes to the current calibration curve resulting from sensor drift since the acquisition of the at least two measured data values used to generate the current calibration curve;
   generating an estimated level value of the analyte level being monitored, based on sensor output from the analyte sensor, in accordance with the predictive calibration curve; and
   causing medicament to be delivered to the patient with a portable infusion pump based on the estimated level value of the analyte being monitored.

2. The method as in claim 1, wherein the transformation function is determined based on a plurality of all calibration curves utilized by the portable medical monitor system beginning at a system start time.

3. The method as in claim 2, wherein the transformation function is determined based on less than all calibration curves utilized by the portable medical monitor system from the system start time through a system time.

4. The method as in claim 2, wherein determining comprises determining a transformation function based on the current calibration curve and an immediately preceding calibration curve such that the determined transformation function substantially produces the current calibration curve when applied to the immediately preceding calibration curve.

5. The method as in claim 1, wherein the transformation function produces a linear regression function of the current calibration curve and the at least one preceding calibration curve.

6. The method as in claim 1, wherein the transformation function produces a polynomial regression function of the current calibration curve and the at least one preceding calibration curve.

7. The method as in claim 1, wherein the at least one preceding calibration curve comprises a default calibration curve that is not based on measured data values of the analyte level being monitored.

8. The method as in claim 1, wherein the portable medical monitor system and portable infusion pump comprise a portable insulin pump, and wherein causing medicament to be delivered to the patient includes actuating a pump mechanism.

9. The method as in claim 1, wherein the analyte being monitored is blood glucose.

10. The method as in claim 1, wherein causing medicament to be delivered to the patient includes transmitting the estimated level value to the portable infusion pump.

11. The method as in claim 1, wherein causing medicament to be delivered to the patient includes transmitting program instructions from the server computer to the portable medical monitor system to transmit the estimated level value to the portable infusion pump.

12. A portable medical monitor system comprising:
an analyte sensor that provides a sensor output value;
a control processor that receives the sensor output value, wherein the processor is configured to execute program instructions stored in memory of the portable medical monitor system to generate a current calibration curve based on at least two measured values of an analyte level of a patient being monitored, to determine a transformation function based on the current calibration curve and at least one preceding calibration curve such that the transformation function produces a predictive calibration curve that predicts changes to the current calibration curve resulting from sensor drift since the acquisition of the at least two measured values used to generate the current calibration curve, and to generate an estimated analyte level value of the analyte being monitored, based on the sensor output value, in accordance with the predictive calibration curve, and
wherein the controller processor is further configured to cause medicament to be delivered to the patient with a portable infusion pump based on the estimated level value of the analyte being monitored.

13. The portable medical monitor system as in claim 12, wherein the control processor determines the transformation function based on a plurality of all calibration curves utilized by the portable medical monitor system beginning at a system start time.

14. The portable medical monitor system as in claim 13, wherein the transformation function is determined based on less than all calibration curves utilized by the portable medical monitor system from the system start time through a current system time.

15. The portable medical monitor system as in claim 1, wherein the control processor determines the transformation function based on the current calibration curve and an immediately preceding calibration curve such that the determined transformation function substantially produces the current calibration curve when applied to the immediately preceding calibration curve.

16. The portable medical monitor system as in claim 12, wherein the transformation function produces a linear regression function of the current calibration curve and the at least one preceding calibration curve.

17. The portable medical monitor system as in claim 12, wherein the transformation function produces a polynomial regression function of the current calibration curve and the at least one preceding calibration curve.

18. The portable medical monitor system as in claim 12, wherein the at least one preceding calibration curve comprises a default calibration curve that is not based on measured data values of the glucose level being monitored.

19. The portable medical monitor system as in claim 12, wherein the portable medical monitor system and the portable infusion pump comprise an insulin pump, and wherein causing medicament to be delivered to the patient includes actuating a pump mechanism.

20. The portable medical monitor system as in claim 12, wherein the analyte being monitored is blood glucose.

21. The portable medical monitor system of claim 12, wherein causing medicament to be delivered to the patient includes transmitting the estimated level value to the portable infusion pump.

22. A method of configuring a portable medical monitor system, the method comprising:
establishing a network communication link at a server computer to the portable medical monitor system;
transmitting program instructions from the server computer to the portable medical monitor system over the network communication link, wherein the transmitted program instructions are configured to be stored in memory of the portable medical monitor system and executed to receive a sensor output value of an analyte sensor and generate a current calibration curve based on at least two measured values of an analyte level of a patient being monitored, to determine a transformation function based on the current calibration curve and at least one preceding calibration curve such that the transformation function produces a predictive calibration curve that predicts changes to the current calibration curve resulting from sensor drift since the acquisition of the at least two measured data values used to generate the current calibration curve, and to generate an estimated analyte level value of the analyte being monitored, based on the sensor output level, in accordance with the predictive calibration curve; and
causing medicament to be delivered to the patient with a portable infusion pump based on the estimated level value of the analyte being monitored.

23. The method as in claim 22, wherein the transformation function is determined based on a plurality of all calibration curves utilized by the portable medical monitor system beginning at a predetermined system start time.

24. The method as in claim 23, wherein the transformation function is determined based on less than all calibration curves utilized by the portable medical monitor system from the system start time through a system time.

25. The method as in claim 23, wherein determining comprises determining a transformation function based on the current calibration curve and an immediately preceding calibration curve such that the determined transformation function substantially produces the current calibration curve when applied to the immediately preceding calibration curve.

26. The method as in claim 22, wherein the transformation function produces a linear regression function of the current calibration curve and the at least one preceding calibration curve.

27. The method as in claim 22, wherein the transformation function produces a polynomial regression function of the current calibration curve and the at least one preceding calibration curve.

28. The method as in claim 22, wherein the at least one preceding calibration curve comprises a default calibration curve that is not based on measured data values of the glucose level being monitored.

29. The method as in claim 22, wherein the portable medical monitor system and the portable infusion pump comprise an insulin pump, and wherein causing medicament to be delivered to the patient includes actuating a pump mechanism.

30. The method as in claim 22, wherein the analyte being monitored is blood glucose.

* * * * *